United States Patent
Kelner

(10) Patent No.: US 9,522,126 B2
(45) Date of Patent: Dec. 20, 2016

(54) TREATMENT OF SKIN AND MUCOSAL SUPERFICIAL WOUNDS USING ADRENERGIC RECEPTOR AGONISTS

(71) Applicant: Roman Kelner, Northbrook, IL (US)

(72) Inventor: Roman Kelner, Northbrook, IL (US)

( * ) Notice: Subject to any disclaimer, the term of this patent is extended or adjusted under 35 U.S.C. 154(b) by 0 days.

(21) Appl. No.: 14/597,017

(22) Filed: Jan. 14, 2015

(65) Prior Publication Data
US 2015/0126556 A1    May 7, 2015

Related U.S. Application Data

(62) Division of application No. 12/243,689, filed on Oct. 1, 2008, now Pat. No. 8,969,331.

(51) Int. Cl.
| | | |
|---|---|---|
| *A61K 31/137* | (2006.01) | |
| *A61K 9/46* | (2006.01) | |
| *A61K 9/00* | (2006.01) | |
| *A61K 31/19* | (2006.01) | |
| *A61K 31/445* | (2006.01) | |
| *A61K 45/06* | (2006.01) | |

(52) U.S. Cl.
CPC .......... *A61K 31/137* (2013.01); *A61K 9/0014* (2013.01); *A61K 31/19* (2013.01); *A61K 31/445* (2013.01); *A61K 45/06* (2013.01)

(58) Field of Classification Search
None
See application file for complete search history.

(56) References Cited

PUBLICATIONS

Stojadinovic, et al., Stress-Induced Hormones Cortisol and Epinephrine Impair Wound Epithelization, 2012, Advances in Wound Care, vol. 1, No. 1, pp. 29-35.*
Kim et al, Catecholamine Stress Alters Neutrophil Trafficking and Impairs Wound Healing by Beta2-Adrenergic Receptor-Mediated Upregulation of IL-6, 2014, Journal of Investigative Dermatology, 134, pp. 809-817.*

* cited by examiner

*Primary Examiner* — Kortney L Klinkel
*Assistant Examiner* — Tori M Strong
(74) *Attorney, Agent, or Firm* — Wood, Phillips, Katz, Clark & Mortimer

(57) ABSTRACT

The invention generally relates to methods of using adrenergic receptor agonists for the treatment of skin and mucosal superficial wounds. Some of the preferred adrenergic receptor agonists include epinephrine, phenylephrine, norepinephrine, methoxamine, and mixtures thereof. Methods according to the invention are especially effective to control superficial skin and mucosal bleeding and accelerate healing time.

9 Claims, 6 Drawing Sheets

TREATMENT OF SKIN AND MUCOSAL SUPERFICIAL WOUNDS USING ADRENERGIC RECEPTOR AGONISTS

FIELD OF THE INVENTION

The invention generally relates to the topical application of adrenergic receptor agonists solutions for the treatment of skin and mucosal superficial wounds. The invention also relates to devices for applying these solutions to the skin or the mucosal area. Methods according to the invention are especially effective to control superficial skin and mucosal bleeding and accelerate healing time.

BACKGROUND OF THE INVENTION

It is well known that many types of sharp objects and abrasives made from various materials in processes of dynamic interaction with skin produce damage to the integrity of skin layers, which results in bleeding from damaged underlying epidermal/hypodermal small blood vessels such as arterioles and capillaries. Rough surfaces, such as asphalt and concrete, in processes of dynamic interaction with skin produce multiple abrasions, limited to the superficial skin layers (epidermis), and characterized by cuts of varying length and penetration. Dynamic interaction of sharp metal objects with skin, like blades, razors or sharp edged glass fragments cause physical damage to skin and underlying tissue in the form of lacerations and cuts. Blind trauma to the nose, lips or cheeks causes secondary rupture of the nasal or oral cavity mucosal layers, and consequently, significant bleeding. Skin abrasions, lacerations, cuts, ruptured mucosal layers of the nasal and oral cavities result in intense and prolonged bleeding from damaged dermal, hypodermal and mucosal small blood vessels, and it is difficult to provide fast and efficient control of the bleeding by traditional methods.

FIG. 1a and FIG. 1b contain illustrations of some types of skin wounds. In both illustrations, the unattractive scabs are clearly visible.

Blood thinning agents used on a daily basis, such as aspirin, Non Steroidal Anti-Inflammatory Drugs (NSAIDs), such as ibuprofen and derivatives, multiple vitamins (in particular, Vitamin E), a variety of herbal mixtures, a wide array of prescribed medications, along with genetic disorders involving factors limiting coagulation, like hemophilia, all contribute to extended bleeding time from skin and mucosal wounds. Skin wounds bleeding continue for an average of 6 to 12 minutes and, as an end result, scab formation takes place.

Superficial and deep damages to skin layers, such as abrasions or lacerations with prolonged healing time under the scab can provoke development of keloid. Dark skin population is more prone to develop keloid. Treatment for keloid is considered to be complex and has varying degrees of effectiveness. Effective bleeding control, absence of scab formation, faster healing process and smaller scar are factors to be considered for prevention of keloid formation.

The prior art methods of controlling bleeding from accidental skin lacerations, cuts or abrasions, along with bleeding from traumatized mucosal layers of the nose and oral cavities, in a home setting or emergency situations, are generally not very efficient and lag behind most modern medical techniques. Usually, to stop bleeding, a locally applied pressure is used for 6 to 12 minutes or until the bleeding stops, by applying absorbent materials (whatever is handy—paper towel, cotton ball, toilette paper, band-aid) and applying redundant continuous pressure on the area.

Thus, formation of a dark brown scab on the superficial skin wound is the end result of the described bleeding control and first aide technique. The scab formation is an unattractive outcome of a superficial and penetrating skin wound from cosmetic point of view. An individual will need to continue the wound care for a prolonged time of 6 to 8 days or even more, if under the scab bacterial inflammation develops. Finally, the wound undergoes a natural self-healing process by developing a newly formed epithelial layer under the scab.

The formation of a thrombotic mass (scab) over the traumatized skin does not stop bleeding; rather it is a form of a rigid protective barrier over the disrupted skin layers. A scab does not guarantee permanent bleeding control to the skin wound; instead, the scab equalizes hydrostatic pressure in damaged small blood vessels (arterioles and capillaries) and surrounding air pressure. Skin wounds may be contaminated by skin saprophytic, environmental, and foreign bodies' bacteria. Bacterial contamination may result in the inflammation under the scab, with pus formation, which complicates and prolongs healing process. Further, the presence of a scab encapsulates contamination agents and prevents clearing of the contamination agents by drainage from the wound's surface. In addition, a scab itself has physical dimensions, which prevents the wound's shrinking and results in the wound's "gapping". Just after trauma, damaged capillary nets are overflown by circulating blood, increasing tension in the surrounding tissue in form of posttraumatic local edema, which is a factor in the wound's "gapping".

Thus, there is a need for new techniques of treating skin wounds that would eliminate scabs' formation, provide sufficient external drainage and accelerate healing time.

BRIEF SUMMARY OF THE INVENTION

The invention generally relates to the surprising discovery that adrenergic receptor agonists, such as epinephrine, and/or phenylephrine, and/or epinephrine and/or methoxamine or a mixture of these compounds, may be used to treat superficial skin and mucosal wounds to control the bleeding and to accelerate healing time after trauma.

In one embodiment, the invention relates to a method for the treatment of superficial skin or a mucosal wound comprising topically applying to the skin or the mucosa a sterile aqueous composition comprising an effective amount of an adrenergic receptor agonist.

In a preferred embodiment, an adrenergic receptor agonist is selected from the group consisting of epinephrine, phenylephrine, norepinephrine, methoxamine, and mixtures thereof.

In a preferred embodiment, the sterile aqueous composition further comprises sodium lactate.

Preferably, the sterile aqueous composition comprises from about 0.001 mg/ml to about 2.5 mg/ml of an adrenergic receptor agonist. In a more preferred embodiment, the aqueous composition is applied at about 0.1 mg/ml concentration of an adrenergic receptor agonist.

In the most preferred embodiment, the sterile composition is a solution which comprises about 0.1 mg/mL of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, about 0.3 mg/mL of sodium lactate, and about 0.75% bupivacaine hydrochloride.

In one embodiment, the sterile aqueous composition is a solution which consists essentially of a) an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent.

In another embodiment, the sterile aqueous composition is a solution which consists essentially of epinephrine hydrochloride, an acidifying agent, and a local anesthetic agent.

In a preferred embodiment, the sterile aqueous composition is a solution which consists essentially of about 0.1 mg/mL of epinephrine hydrochloride, about 0.3 mg/mL of sodium lactate, and about 0.75% bupivacaine hydrochloride.

In another embodiment, the sterile composition is a solution which consists essentially of about 0.1 mg/mL of epinephrine hydrochloride and/or 0.1 mg/ml of phenylephrine hydrochloride and/or 0.1 mg/ml of norepinephrine hydrochloride, and/or methoxamine hydrochloride, and/or a mixture thereof, about 0.3 mg/mL of sodium lactate, and about 0.75% bupivacaine hydrochloride.

The invention also relates to a disposable dispenser that may be used to deliver the compositions of the present invention.

In one embodiment, the disposable dispenser comprises a cap cover, a sponge cap, a hollow shaft with a perforator, and a dispensing part which comprises a sterile solution comprising a) an effective amount of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent.

In another embodiment, the invention also relates to an applicator that comprises a sealed aluminum foil or thin plastic pouch, wherein said sealed aluminum foil or thin plastic pouch comprises a sterile solution comprising a) an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent, and a synthetic applicator, and wherein said synthetic applicator is soaked in said sterile solution.

DETAILED DESCRIPTION OF THE INVENTION

Figure 1A:
FIG. 1a is a prior art illustration of a skin laceration with a scab formation.
Figure 1B:
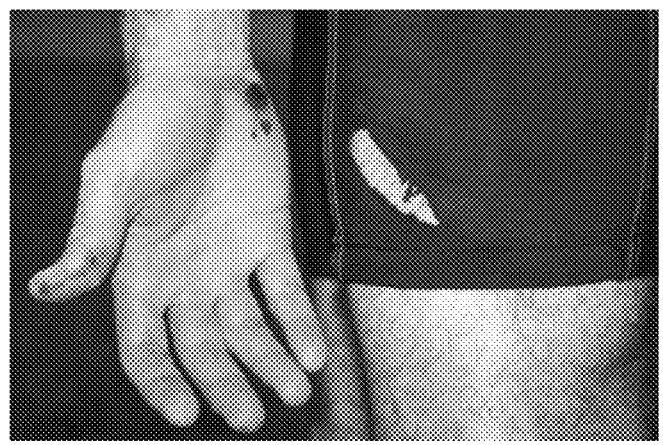
FIG. 1b is a prior art illustration of a skin abrasion with a scab formation.

The invention is generally based on the surprising discovery that an adrenergic receptor agonist may be used to treat superficial skin and mucosal wounds to control the bleeding and to accelerate healing time after trauma. The preferred adrenergic receptor agonists are selected from the group consisting of epinephrine, phenylephrine, norepinephrine, methoxamine, and mixtures thereof.

Epinephrine is a neurotransmitter hormone. Its chemical formula is:

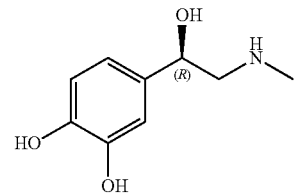

Epinephrine is a water soluble catecholamine that is catabolized to the inactive compound metanephrine through the sequential actions of catecholamine-O-methyltransferase (COMT) and monoamine oxidase (MAO) (See, Champe, Pamela, and Richard Harvey, eds. Biochemistry. Philadelphia: Lippincott-Raven Publishers, 1994, at 266). Epinephrine is commercially available in the United States and abroad. Epinephrine activates α1, α2, β1, and β2 adrenergic receptors.

Phenylephrine or Neo-Synephrine is an α1-adrenergic receptor agonist. It is also a vasoconstrictor.

Norepinephrine activates α1, α2, and β1 adrenergic receptors. It is also a vasoconstrictor.

Methoxamine is a direct-acting α1 and α2 adrenergic receptor agonist. It is also a vasoconstrictor.

As used in this application, the terms "adrenergic receptor agonist," "epinephrine," "phenylephrine," "norepinephrine," and "methoxamine" include the pharmaceutically acceptable salts of these compounds. For example, the term "epinephrine" includes "epinephrine hydrochloride."

While not wishing to be bound to any specific theory, it is possible that an adrenergic receptor agonist (e.g. epinephrine or phenylephrine, or norepinephrine, or methoxamine) is efficacious in treating superficial skin and mucosal wounds because, when topically applied, an adrenergic receptor agonist solution enters only through damaged skin by means of diffusion, penetrates into the hypodermis through interstitial space, and binds to α1-adrenergic receptors located on postarteriolar precapillary sphincters, it initiates a chain response through the activation of G-protein coupled receptors (GPCRs). When an adrenergic receptor agonist binds to the α1-adrenergic receptor, a conformational change in the transmembrane protein activates the G-protein which is located in the muscle elements of arterioles and precapillary sphincters of the arteriole-venal capillary nets. Activation of α1-adrenoreceptors stimulates intracellular response by increased production of DAG (diacylglycerol) and IP3 (inositoltriphosphate) leading to an increase in intracellular (endo/sarcoplasmic reticulum) Ca2+ ions (Harvey, Richard, and Pamela Champe, eds. Pharmacology, Philadelphia: J.B. Lippincott Company, 1992, at 62). The $Ca^{2+}$ ions stimulate contraction of muscle elements in the arterioles and postarteriolar precapillary sphincters, effectively blocking blood flow in and out of the damaged capillaries. Thus, blood flow trough arteriolar-venal capillary net is effectively blocked, and transport of blood clot forming elements is halted, preventing formation of thrombotic mass (i.e., scab). This temporary block of blood flow through the local capillary net leads to relative shrinkage of the skin around the wound which decreases the wound's "gapping" and results in local whitening of the skin in the area adjacent to the topical epinephrine application. After about fifteen to twenty minutes, the white color of the skin reverts back to the individuals' normal skin color, as a result of epinephrine's short half-life, and rapid biodegradation.

Epinephrine, phenylephrine, norepinephrine, and methoxamine cannot penetrate healthy, not damaged skin.

One of the advantages of the present invention is that it does not require any other active ingredients in addition to an adrenergic receptor agonist. Another advantage of the present invention is that it does not require the use of any lubricants. Yet another advantage of the present invention is that it does not require the use of any toxic components; the amounts of topically used adrenergic receptor agonists are non-toxic. The compositions used in the present invention are also non-allergic. Finally, the methods of the present invention do not involve raising the temperature of the solutions; they are applied at a normal human body temperature.

Thus, in one embodiment, the invention relates to a method for the treatment of a superficial skin or a mucosal wound comprising topically applying to the skin or the mucosa a sterile aqueous composition comprising an effective amount of an adrenergic receptor agonist.

In a preferred embodiment, an adrenergic receptor agonist is selected from the group consisting of epinephrine, phenylephrine, norepinephrine, methoxamine, and mixtures thereof.

In a preferred embodiment, the sterile aqueous composition further comprises sodium lactate.

In another embodiment, the invention relates to a method for the treatment of a superficial skin or a mucosal wound comprising topically applying to the skin or the mucosa a sterile composition consisting essentially of an effective amount of an adrenergic receptor agonist, wherein said adrenergic receptor agonist is selected from the group consisting of epinephrine, phenylephrine, norepinephrine, methoxamine, and mixtures thereof.

In another embodiment, the invention relates to a method for the treatment of a superficial skin or a mucosal wound comprising topically applying to the skin or the mucosa a sterile composition consisting essentially of a) an effective amount of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent.

In another embodiment, the invention relates to a method for the treatment of a superficial skin or a mucosal wound comprising topically applying to the skin or the mucosa a sterile composition consisting essentially of an effective amount of epinephrine hydrochloride, an acidifying agent, and an anesthetic agent.

In another embodiment, the invention relates to a method for the treatment of a superficial skin or a mucosal wound comprising topically applying to the skin or the mucosa a sterile composition consisting essentially of an effective amount of norepinephrine and phenylephrine, an acidifying agent, and an anesthetic agent.

In another embodiment, the invention relates to a method for the treatment of a superficial skin or a mucosal wound comprising topically applying to the skin or the mucosa a sterile composition consisting essentially of an effective amount of norepinephrine and methoxamine, an acidifying agent, and an anesthetic agent.

The term "wound" is used broadly and is meant to include abrasions, lacerations, cuts, and the like.

The terms "effective amount of an adrenergic receptor agonist", "effective amount of epinephrine," "effective amount of norepinephrine," "effective amount of methoxamine," and "effective amount of phenylephrine" refer to a sufficient amount of an adrenergic receptor agonist or epinephrine, or phenylephrine, or norepinephrine, or methoxamine to treat wounded skin or mucosa and produce a desired effect, i.e. to stop bleeding and to prevent formation of a scab. The effective amount of an adrenergic receptor agonist, or epinephrine, or phenylephrine, or norepinephrine, or methoxamine is not fixed per se, and is dependent on many factors, including, but not limited to, the severity, extent, and nature of the wound treated; the patient's skin type; the amount of adjunct ingredients in the composition. The effective amount of an adrenergic receptor agonist, or epinephrine, or phenylephrine, or norepinephrine, or methoxamine is usually at least about 0.001 mg. It is well within the skill of the art to arrive at the correct amount without undue experimentation.

In some typical embodiments, the compositions employed in the methods of the invention comprise from about 0.001 mg/ml to about 1 mg/ml of an adrenergic receptor agonist selected from the group consisting of epinephrine, phenylephrine, norepinephrine, methoxamine, and mixtures thereof, and more preferably from about 0.01 mg/ml to about 2.5 mg/ml of an adrenergic receptor agonist selected from the group consisting of epinephrine, phenylephrine, norepinephrine, methoxamine, and mixtures thereof.

In a more preferred embodiment, the adrenergic receptor agonist composition is applied at about 0.1 mg/ml concentration of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, about 0.3 mg/mL of sodium lactate, and about 0.75% bupivacaine hydrochloride.

In another preferred embodiment, about 0.06 mg of epinephrine and/or phenylephrine and/or norepinephrine and/or methoxamine is applied to a superficial skin or mucosal wound, wherein the area of the wound is up to 30.0 mm2.

The compositions may be administered in a pharmaceutically acceptable carrier suitable for topical delivery.

The compositions also preferably comprise an anesthetic agent, selected from the group consisting of bupivacaine, lidocaine, chloroprocaine, dibucaine, etidocaine, tetracaine, procaine, and mixtures thereof.

The compositions also preferably comprise an acidifying agent, selected from the group consisting of sodium citrate, potassium citrate, sodium lactate, and mixtures thereof.

In one embodiment, the sterile aqueous composition is a solution which consists essentially of a) an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent.

In another embodiment, the sterile aqueous composition is a solution which consists essentially of epinephrine hydrochloride, an acidifying agent, and a local anesthetic agent.

In another embodiment, the sterile aqueous composition is a solution which consists essentially of methoxamine hydrochloride, an acidifying agent, and a local anesthetic agent.

In a preferred embodiment, the sterile aqueous composition is a solution which consists essentially of about 0.1 mg/mL of epinephrine hydrochloride, about 0.3 mg/mL of sodium lactate, and about 0.75% bupivacaine hydrochloride.

In another embodiment, the sterile composition is a solution which consists essentially of about 0.1 mg/mL of epinephrine hydrochloride and/or 0.1 mg/ml of phenylephrine hydrochloride and/or 0.1 mg/ml of norepinephrine hydrochloride, and/or 0.1 mg/ml of methoxamine hydrochloride, and/or a mixture thereof, about 0.3 mg/mL of sodium lactate, and about 0.75% bupivacaine hydrochloride.

The methods of the present invention preferably lower the wound's area pH to about 4.5 to about 6.5, more preferably to about 5.5 to about 6.5, most preferably to about 6.0 to about 6.5. Thus, methods of the present invention preferably result in an acidification of the wound area, which has an antibacterial effect.

In a preferred embodiment, the methods of the present invention efficiently control bleeding with no scabbing, lower the wound's area pH to about 6.5, and provide a local anesthetic in minute quantities to provide temporary local pain relieve.

According to the methods of the present invention, healing of the superficial skin or mucosal wounds, lacerations or abrasions proceeds through its natural course, but takes less time to complete the process. For example, if the methods of the present invention are employed, it may take about 2-3 days to heal the small cut, in comparison to about 6-8 days through its natural course. It is believed that less time is required for healing of the superficial wounds because the wound "gapping" is significantly smaller and faster formation of the new epithelial layers does not proceed under the scab and the acidic pH prevents local bacterial grows. Absence of a scab does not limit function of the treated local area and consequently promotes healing. Accordingly, no time is needed to soften up and slough off the scab, and keratinization processes are accomplished faster. In addition, the smooth alignment of the wound edges leads to more discreet scarring, which is cosmetically favorable.

Compositions containing from about 0.001 mg/ml to about 2.5 mg/ml of epinephrine promoted healing of small cuts and/or abrasions when applied topically, leading to quicker wound resolution than that observed on untreated or treated with conventional methods wounds; and faster control of bleeding. Further, no scabs were formed visually on skin areas treated with the inventive compositions. It is believed that if phenylephrine, and/or norepinephrine, and/or methoxamine, and/or mixtures thereof were used instead of, or together with, epinephrine, the result would have been the same or even amplified.

Wound- and scar-reducing topical compositions of the invention can comprise additional ingredients commonly found in skin care compositions, such as, for example, emollients, skin conditioning agents, emulsifying agents, humectants, preservatives, antioxidants, perfumes, chelating agents, etc., provided that they are physically and chemically compatible with other components of the composition.

Buffering agents may also be employed in the compositions and methods of the present invention. Preferably, the amount of buffering agent is one that results in compositions having a pH ranging from about 4.5 to about 6.5, more preferably from about 5.5 to about 6.5, most preferably from about 6.0 to about 6.5. Typical buffering agents are chemically and physically stable agents commonly found in cosmetics, and can include compounds that are also adjunct ingredients such as citric acid, malic acid, and glycolic acid buffers.

Disposable Dispenser

In another embodiment, the invention relates to a disposable dispenser that can be used to apply the compositions of the claimed methods to the skin wound area.

Figure 2A:
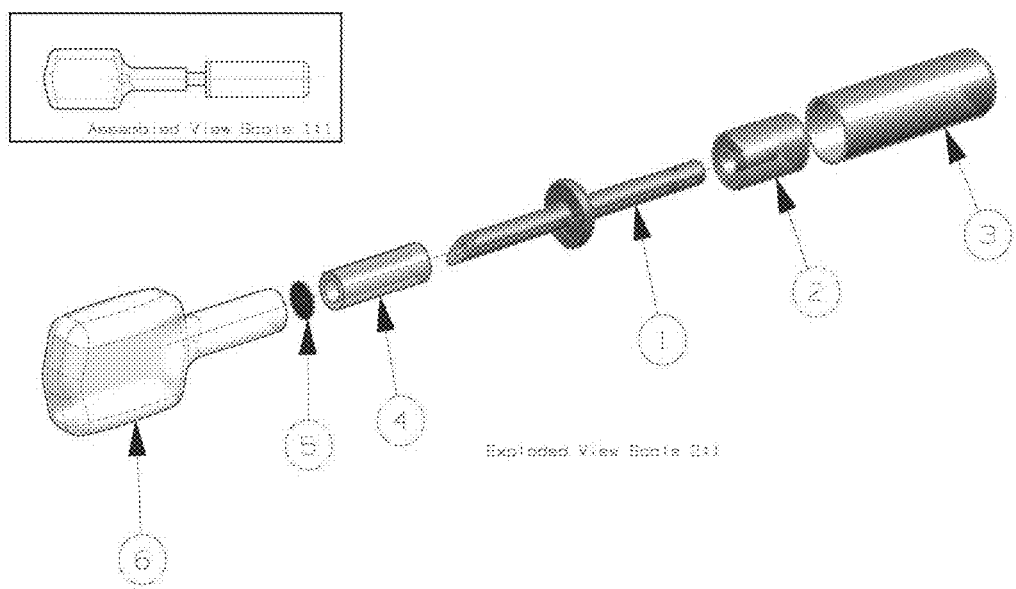
FIG. 2a is an illustration of a disposable dispenser comprising an adrenergic receptor agonist solution.

FIG. 2a is an illustration of a disposable dispenser comprising a) an effective amount of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent.

The disposable dispenser preferably comprises the following parts: a cap cover (3), a sponge cap (2), a hollow shaft with a perforator (1), an aluminum foil membrane (4), and a dispensing part comprising a sterile solution (6).

The disposable dispenser is preferably made of plastic or other synthetic material.

In one embodiment, the dispensing part comprises three fused together parts:
  a) a plastic cylinder,
  b) an aluminum foil membrane, and
  c) a plastic container for a sterile solution comprising epinephrine or phenylephrine.

Typically, an aluminum foil membrane is placed at the top of the container, sealing the sterile content, and to guarantee the sterility of the dispenser's contents. The plastic container is preferably made of opaque and/or non-transparent flexible plastic to prevent deactivation of an adrenergic receptor agonist by direct light. The plastic container is securely attached to the bottom part of the plastic cylinder.

It is to be understood that the illustration is solely to explain the principle of this aspect of the invention; a skilled artisan would be able to make obvious modifications and variations (for example, to use a different scale) to the device.

Figure 2B:
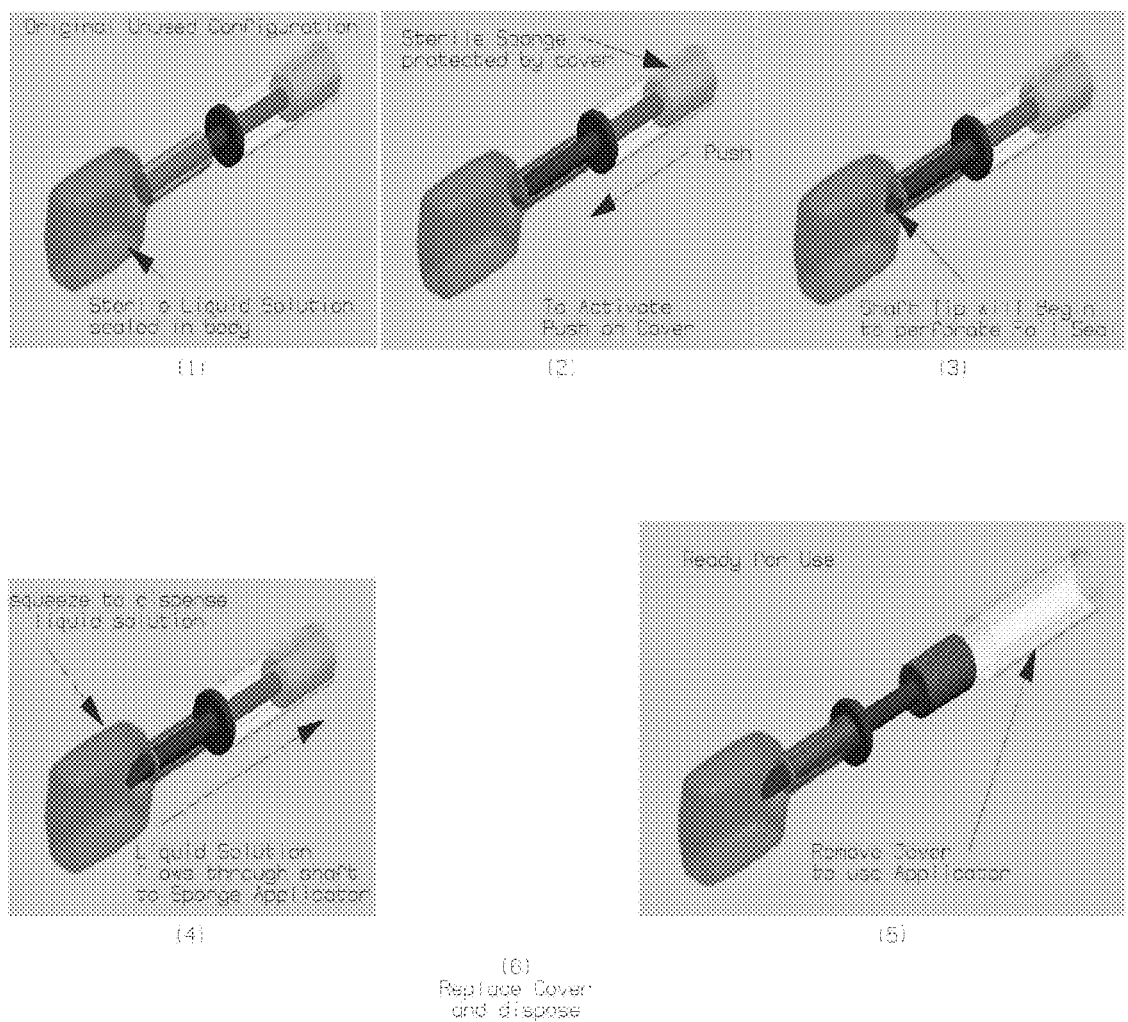
FIG. 2b is a schematic illustration of the mode of action of the disposable dispenser.

FIG. 2b is a schematic illustration of the mode of action of the disposable dispenser according to one aspect the present invention.

In (1), the original unused configuration is depicted. The sterile liquid solution comprising a) an effective amount of an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent is sealed in the dispensing part.

In (2), the dispenser is "activated" by pushing the applicator's cap cover down toward the fluid container by linear or rotating movement. The cap cover prevents contamination of the sterile applicator's cap before use, and sets up in motion the applicator's tube.

In (3), the perforator end penetrates through the aluminum foil membrane, allowing the sterile adrenergic receptor agonist solution to flow toward the sponge cap.

In (4), the sterile adrenergic receptor agonist solution flows through the hollow shaft to the sponge cap.

In (5), the cap cover is removed and the dispenser is ready to use.

The adrenergic receptor agonist solution, preferably comprising an acidifying agent and local anesthetic agent, is released through the cap for topical application on the skin wound's surface or mucosal surface in the nasal or oral cavities. The cap tip's surface provides ability to apply the sterile adrenergic receptor agonist solution in a precise fashion to the areas up to 10.0 $mm^2$.

The elongated design of the applicator provides easy access to the bleeding nasal, oral cavity mucosa, deep penetrating, punctured wounds, anal and vaginal areas. The applicator cap's sides provide coverage area up to 30.0 mm2 of wound surface.

The application time is generally up to ten seconds, which is the time needed to achieve bleeding control. The adrenergic receptor agonist solution application should be ended when the bleeding stops and the skin around the wound "whitens." The overexposure to the adrenergic receptor agonist solution would not provide any additional absorption either through the wound or through the intact surrounding skin.

Figure 2C:
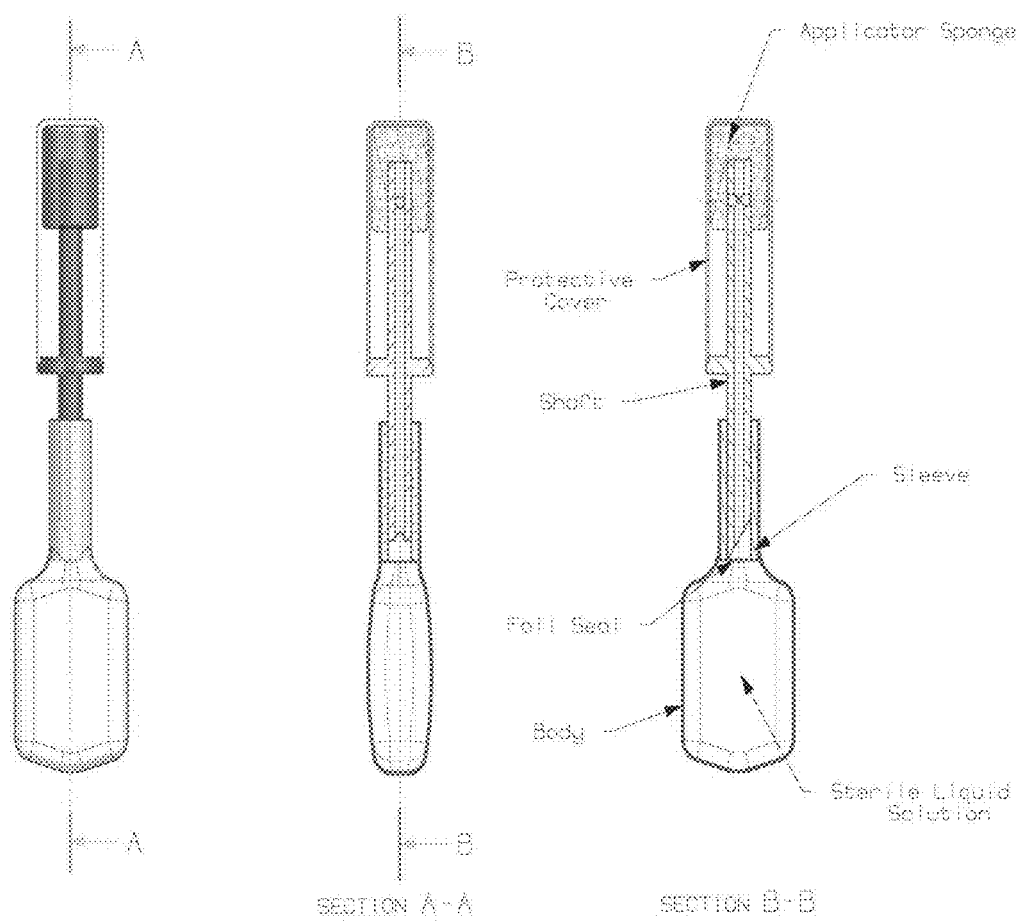
FIG. 2c is an example of a cross-sectional view of the disposable dispenser.

FIG. 2c is an example of a cross-sectional view of the disposable dispenser. It is provided for illustrative purposes only and is not intended to limit the scope of the invention.

Disposable Applicator

In another embodiment, the invention relates to a disposable applicator that can be used to apply the compositions of the claimed methods to the skin wound area.

In one embodiment, the applicator comprises a sealed aluminum foil or thin plastic pouch, wherein said sealed aluminum foil or thin plastic pouch comprises a sterile solution comprising a) an adrenergic receptor agonist, wherein said adrenergic receptor agonist is selected from the group consisting of epinephrine hydrochloride, phenylephrine hydrochloride, norepinephrine hydrochloride, methoxamine hydrochloride, and mixtures thereof, b) an acidifying agent, and c) a local anesthetic agent, and a synthetic applicator, and wherein said synthetic applicator is soaked in said sterile solution.

Figure 3A:
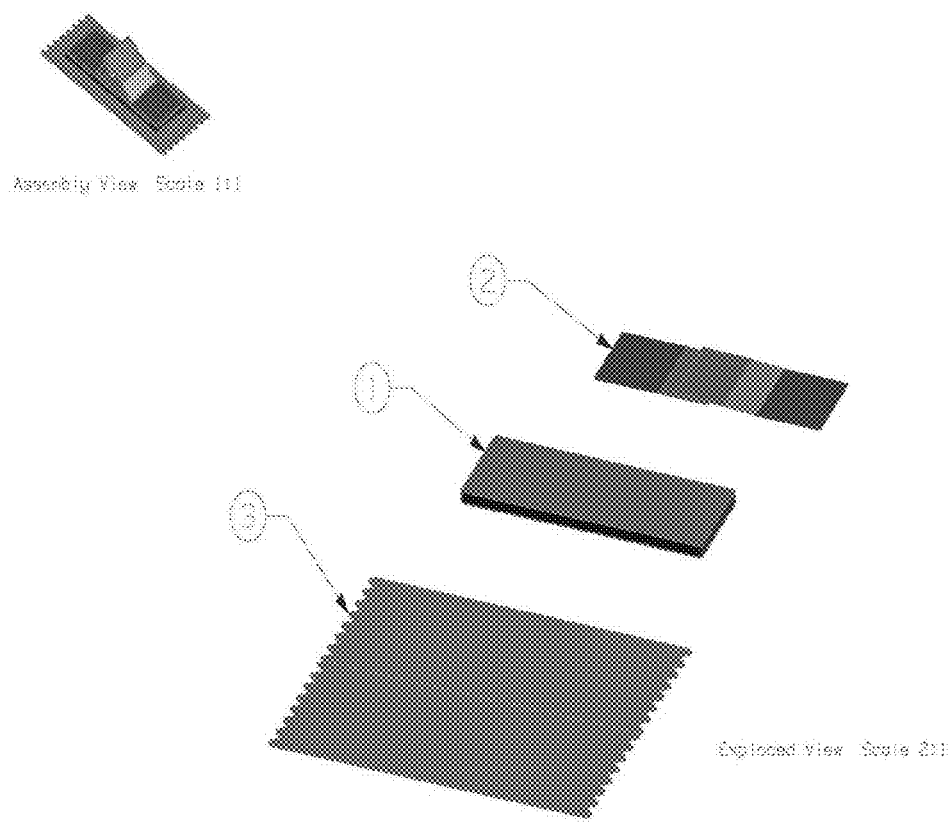
FIG. 3a is an illustration of an applicator comprising an adrenergic receptor agonist solution.

FIG. 3a is an illustration of the disposable applicator. The applicator comprises the following parts: an aluminum foil or thin plastic wrapper pouch (3), a grip strip (2), and a sterile fabric (1). The sterile fabric (1) is pre-soaked in a sterile solution comprising the solutions according to the present invention. The grip strip is made of synthetic material and is thermo-fused to the sterile fabric.

Figure 3B:
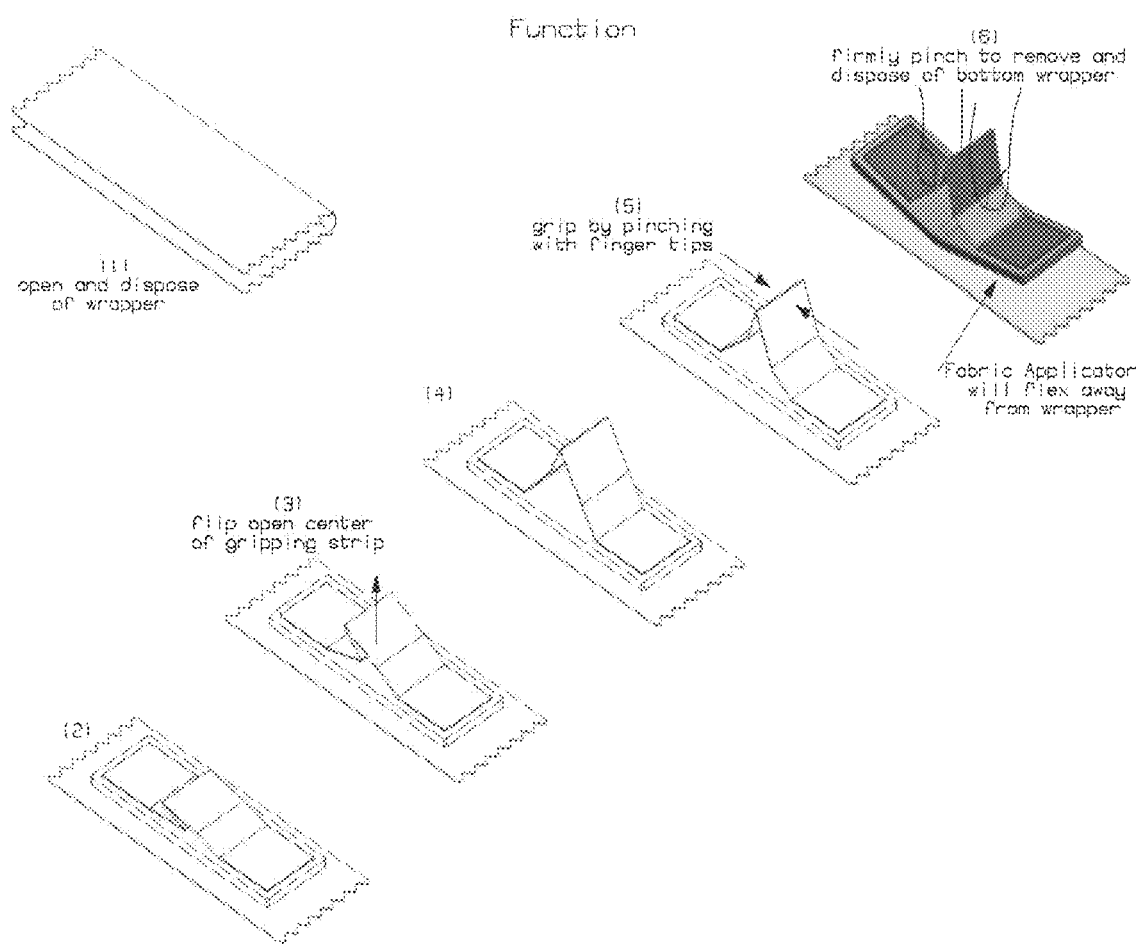
FIG. 3b is a schematic illustration of the mode of action of the applicator.

FIG. 3b is a schematic illustration of the mode of action of the applicator.

At the starting point, the grip strip and the sterile fabric are enclosed in the sealed aluminum foil or thin plastic pouch. The pouch contains a sterile solution according to the present invention, preferably at a concentration of about 0.1 mg/ml. In a preferable embodiment, the sterile solution comprises epinephrine and/or phenylephrine and/or norepinephrine, and/or methoxamine or a mixture thereof, sodium lactate, and bupivacaine hydrochloride. In another preferable embodiment, the total volume of the solution is about 1.2 ml.

The applicator is activated by tear-opening the aluminum foil or thin plastic wrapper. Then, the grip strip is grabbed at around the center; which unfolds the strip and rolls up the applicator's edges to ensure that the bottom part of the applicator remains sterile.

The unfolded strip provides an easy and convenient way to apply the applicator pre-soaked in the sterile solution to the wounded surface. The applicator provides coverage area up to about 30.0 mm2 of wound surface. The application time is up to about 10 seconds, which allows to achieve bleeding control, local anesthetic effect, and antibacterial acidification of the wound. The adrenergic receptor agonist application should be ended when the bleeding stops and the skin around the wound "whitens."

As used in the specification and the claims, all numerical values relating to amounts, weight percentages, and the like are defined as "about" or "approximately" each particular value, plus or minus 10%. Therefore, amounts within 10% of the claimed values are encompassed by the scope of the claims.

As used in the specification and the claims, the singular forms "a," "an," and "the" include plural referents unless the context clearly dictates otherwise.

The above description is for the purpose of teaching the person of ordinary skill in the art how to practice the present invention, and it is not intended to detail all those obvious modifications and variations of it which will become apparent to the skilled artisan upon reading the description. It is intended, however, that all such obvious modifications and variations be included within the scope of the invention in any sequence which is effective to meet the objectives there intended, unless the context specifically indicates the contrary.

What is claimed is:

1. A method for the treatment of a superficial skin or a mucosal wound comprising topically applying to the skin or the mucosa a sterile aqueous composition comprising an effective amount of epinephrine.

2. The method of claim 1, wherein said sterile aqueous composition comprises from about 0.001 mg/ml to about 2.5 mg/ml of epinephrine.

3. The method of claim 1, wherein the skin or the mucosal wound is an abrasion or a cut.

4. The method of claim 1, wherein the skin or the mucosal wound is a laceration.

5. The method of claim 1, wherein said method inhibits blood flow in the local arteriolar-venal capillary nets.

6. The method of claim 1, wherein said method results in shrinkage of the skin or the mucosa around said skin or said mucosal wound.

7. The method of claim 1, wherein said sterile composition is applied using a disposable dispenser.

8. The method of claim 1, wherein said sterile composition is applied using a disposable solution applicator.

9. The method of claim 1, wherein the treatment results in the absence of a scab.

\* \* \* \* \*